United States Patent [19]

Corsich

[11] Patent Number: 5,250,030
[45] Date of Patent: Oct. 5, 1993

[54] HYPODERMIC SYRINGE WITH A BLOCKABLE PISTON CAPABLE OF PREVENTING ITS RECHARGE AND REUSE

[76] Inventor: César G. Corsich, 1462 Juan A. García St., Del Viso, Buenos Aires Province, Argentina

[21] Appl. No.: 784,560

[22] Filed: Oct. 29, 1991

[30] Foreign Application Priority Data

Oct. 3, 1991 [AR] Argentina .............. 320846

[51] Int. Cl.$^5$ .............................. A61M 5/00
[52] U.S. Cl. ........................ 604/110; 604/210; 604/218
[58] Field of Search ............ 604/110, 207, 208, 210, 604/220, 187, 209, 211, 218

[56] References Cited

U.S. PATENT DOCUMENTS

| | | | |
|---|---|---|---|
| 4,840,616 | 6/1989 | Banks | 604/110 |
| 4,978,339 | 12/1990 | Labouze et al. | 604/110 |
| 5,024,661 | 6/1991 | Wender et al. | 604/110 |
| 5,084,017 | 1/1992 | Maffetone | 604/110 |

*Primary Examiner*—C. Fred Rosenbaum
*Assistant Examiner*—C. Maglione
*Attorney, Agent, or Firm*—Emrich & Dithmar

[57] ABSTRACT

Hypodermic syringe with a blockable piston capable of preventing it recharge and reuse, comprising a cylindrical tubular body having a communicating container in its inlet end; a right-angled section piston rod; a first blocking means constituted by at least one member placed in abutment against rotation over the container bottom and opposed alternatively to on and the other of toothed intermediate sections of the piston rod; and a second blocking means slidingly mounted over the piston rod, placed in abutment with the first blocking means and urged in positional fastening by an elastic retention member constituting in turn, the lid of the container.

19 Claims, 1 Drawing Sheet

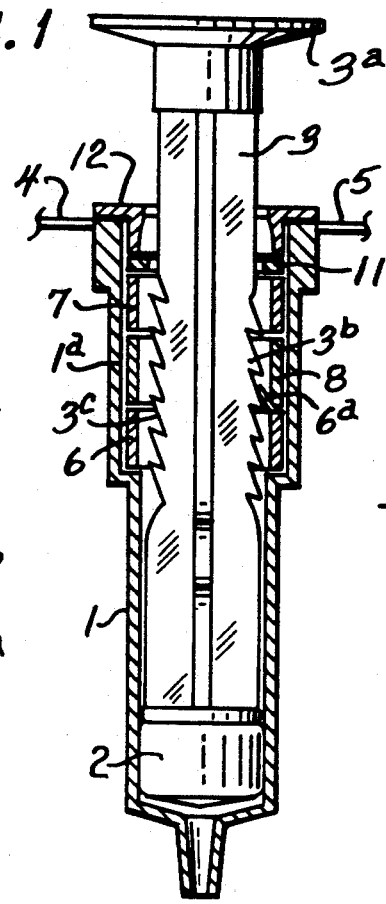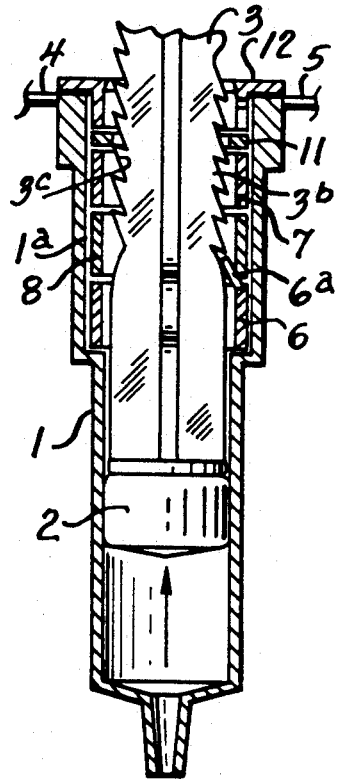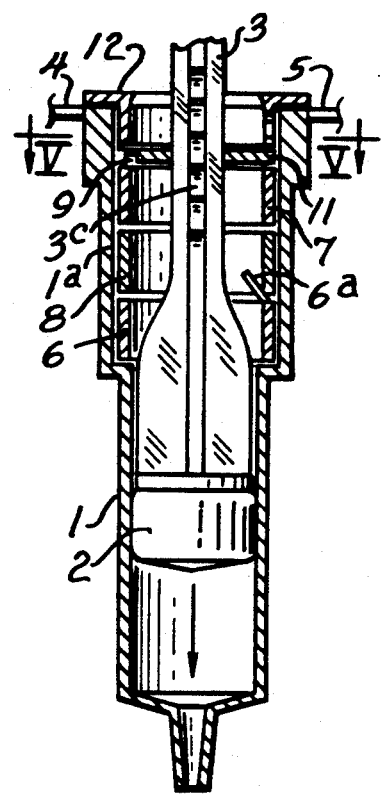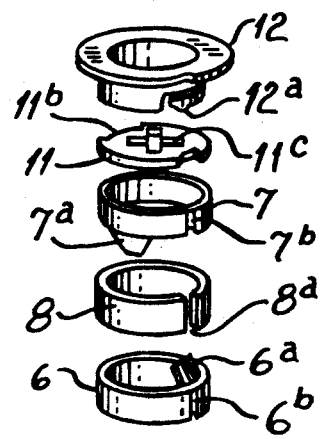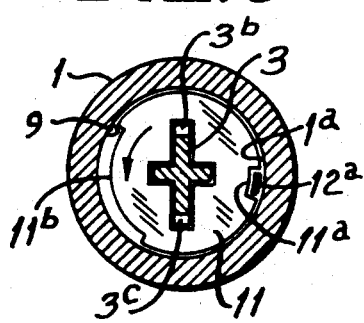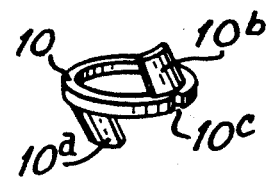

HYPODERMIC SYRINGE WITH A BLOCKABLE PISTON CAPABLE OF PREVENTING ITS RECHARGE AND REUSE

BACKGROUND OF THE INVENTION

The present invention relates to a hypodermic syringe with a blockable piston capable of preventing its recharge and reuse.

It is generally known that certain diseases, such as AIDS (Acquired Immune Deficiency Syndrome) and some kinds of hepatitis, can be acquired by sharing hypodermic syringes.

Consequently, it is usually recommended to use discardable syringes which, regretfully and due to the fact that they may be recharged and reused by irresponsible people, do not afford a definitive solution to the problem.

SUMMARY OF THE INVENTION

In order to solve the cited problem, the hypodermic syringe of the present invention provides an important advance, mainly based on the fact of its impossible recharge and reuse, which is achieved practically and simply, by a piston placed with respect to blocking means capable of preventing every movement after the only possible injection has been dispensed.

The syringe of the present invention includes, in the inlet end of its cylindrical tubular body, a housing or container portion for the blocking means which, in a more specific manner, will act with respect to the right-angled section piston rod, and apart from collaborating with either toothed sections of the edges of two of its wings, carries slidingly mounted thereon one of the blocking means which, combined with another one, in its turn constituting a static cap applied over the inlet mouth for the housing, is nonspinning. The remaining members act to prevent the reverse displacement of the piston, but only after facilitating such movement for charging the syringe and, by means of an approximately 90° turn of the same piston over its rod, to effect its own advance movement with the single injection.

Bearing in mind its constructive features and in order to disclose the true inventive scope of the present hypodermic syringe, it may be stated that it comprises the combination of a cylindrical tubular body having a container portion in its inlet end; a right-angled section piston rod, two of its opposed wings longitudinal edges having intermediate sections that are toothed as per relatively opposed slopes, and housed within the container; a blocking means constituted by at least one member, placed in abutment against rotation over the container bottom and opposed alternatively to one and the other toothed intermediate sections of the piston rod, first for the advance of the piston with the syringe already filled and then, through the 90° turn of the rod, for the reverse movement of said piston; and another blocking means securing said rotating position, slidingly mounted over the piston rod, placed in abutment with the first blocking means and urged in positional fastening by an elastic retention member, constituting in turn a lid integrally placed over the container mouth.

BRIEF DESCRIPTION OF THE DRAWINGS

In order for the present invention to be better and more clearly understood, it will be hereinafter described in detail and with reference to the accompanying drawings, in which a preferred and not limitative embodiment is shown.

FIG. 1 is a transverse view of the invented syringe with its piston and blocking means in idle position;

FIG. 2 is a view similar to FIG. 1 but shortened and with the piston in the position corresponding to its reversal for filling and blocking;

FIG. 3 is a view similar to FIG. 2 but showing the descent or forward movement of the piston after unblocking by means of a 90° turn, under the action of its own rod;

FIG. 4 is a perspective view of the members constituting the blocking means;

FIG. 5 is a diametrical view of the syringe through the V—V section indicated in FIG. 3; and FIG. 6 shows in perspective a modified embodiment of the blocking means opposed to the forward and rearward displacement of the syringe piston.

In the cited drawings, the same reference numerals indicate similar or corresponding parts.

DETAILED DESCRIPTION

The hypodermic syringe according to the present invention comprises a cylindrical tubular body 1 and a piston 2 located within the tubular body, and displaceable axially under push-and-pull action. The piston has a projecting rod 3 which terminates in a handle 3a opposed to catching lugs 4 and 5 which, in turn, project opposite and coplanarly from the mouth of the body 1.

The body 1 of the syringe defines, in its inlet portion, a chamber 1a for receiving a substance to be dispensed by the syringe. Rod 3 of piston 2 is of a right-angled section, with a first pair of its opposed wings being longer than the other pair of wings. The intermediate sections of the longitudinal edges of the first pair of wings have teeth 3b and 3c respectively sloped in opposite directions. The teeth are located within the container 1a when the syringe is in its idle condition and the piston is in its maximum extension or rest position.

Within the chamber 1a, blocking means are located in operative relationship with rod 3 of piston 2, for preventing both axial and rotational movement of the latter, in order to make impossible the refilling and reuse of the syringe which, then, must be rejected after its first and only use.

According to the embodiment shown in FIGS. 1 to 5, the blocking means comprise a pair of rings 6 and 7 separated by spacer 8 and having respective blocking lugs 6a and 7a, which cooperate with respective teeth 3b and 3c for preventing the axial displacement of piston 2 when needed. Both of the rings 6 and 7 and spacer 8 are held against rotation by means of the rib 9 provided on the inner wall of the chamber 1a, the rib 9 being received in respective longitudinal notches 6b and 7b of the rings and the split 8a of the spacer.

However, optionally, a single annular member 10 (FIG. 6) can replace both rings 6 and 7 and perform a similar blocking action, because it has a pair of lugs 10a and 10b for the same purpose as lugs 6a and 7a, and include a notch 10c corresponding to notches 6b and 7b.

Finally, overlying the already described ring 7, is a disc-shaped member 11, having a "cross-shaped" central opening 11c, and slidingly mounted on rod 3 of piston 2. Member 11 ensures a 90° rotation of the piston 2 and rod 3. A lid or cap 12 is also a part of body 1 of the syringe and is located to close the mouth thereof. Cap 12 presents a circularly slitted elastic or resilient skirt having a tooth 12a located to enter into a radial slit 11a of the disc-shaped member 11. Member 11 includes an abutment notch 11b which cooperates with rib 9 of the chamber 1a to limit rotation of member 11 to approximately 90°.

The above disclosed syringe operates as follows: when it is to be filled, the user grasps handle 3a and draws piston 2 in a reverse direction (FIG. 2). Lug 6a rides on the backsides of teeth 3b so that the lug 6a fails to engage teeth 3b in a manner to prevent axial movement of the piston, permitting a substance to be dispensed to be drawn into the chamber. The blocking lug 7a of ring 7 is displaced circumferentially approximately 90° with respect to the lug 6a and is thus displaced from teeth 3b and teeth 3c and engages the smooth edge of the corresponding small wing of the rod 3 of piston 2. Once the syringe has been filled up with the substance to be dispensed, advance movement of said piston 2 (FIG. 3) is prevented by the blocking lug 6a which engages teeth 3b. For this reason, to permit the piston to be advanced to its extended position to dispense the substance contained in the chamber, it is necessary that the user rotate the piston by rotating the handle 3a of its rod 3 to free lug 6a from the teeth 3b, simultaneously move lug 7a of ring 7 to operative relationship with teeth 3c. Such relationship is necessary for preventing axial movement in the opposite direction of the piston, bearing in mind that, for any attempt of doing so, blocking of or engagement of lug 7a with tooth 3c will occur. As handle 3a is rotated, the disc-shaped member 11 will also be rotated 90° until abutment of its notch 11b with rib 9 at which position its radial slit 11a is located below tooth 12a of the lid-cap 12 allowing tooth 12a, by virtue of its resilience, to flex into slit 11a, so as to be blocked against rotation because tooth 12a penetrates thereinto. Thus, once the syringe has been used, the piston cannot be withdrawn because of the blocking action of member 11, preventing rotational movement of the piston, and of the blocking action of lug 7a and teeth 3c, preventing axial movement of the piston.

I claim:

1. A hypodermic syringe with a blockage piston capable of preventing its recharge and reuse, comprising, in combination: a cylindrical tubular body; a piston means including a piston located within the cylindrical tubular body and having a right-angled piston rod section associated therewith, said piston means being movable axially of the tubular body in one direction to retract the piston for drawing a substance into said tubular body; said right-angled piston rod section including a pair of intersecting opposed wings, the longitudinal outward edges of one of said pair of intersecting opposed wings having intermediate sections which include tooth shaped portions, with each tooth shaped portion defining opposed indentation slopes thereof with said intermediate sections located within the tubular body; a blocking means positioned within said cylindrical tubular body and engageable with said tooth shaped portions of said longitudinal outward edges of said intermediate section of said piston rod section, said blocking means constituted by at least one member placed in abutment against rotation with respect to said tubular body and cooperating with said tooth shaped portions of the piston rod for permitting the advancement of the piston rod axially outwardly of said tubular body, and, after a 90° turn of the piston rod, axial inward movement of said piston rod into said tubular body; and locking means including a first member slidably mounted on and operatively associated with said pair of opposed wings of said piston rod to be rotated thereby through said 90° turn of said piston rod to a locking position to prevent further rotation of said piston rod relative to said tubular body.

2. The hypodermic syringe according to claim 1, characterized in that the other pair of intersecting opposed wings of said piston rod section possess a radial diameter less than said one of said pair of wings.

3. The hypodermic syringe according to claim 1, characterized in that said blocking means comprises first and second angular members having respective first and second blocking lugs and a spacer interposed between said first and second angular members.

4. The hypodermic syringe according to claim 1, characterized in that said blocking means comprises an angular member with a pair of lugs related to each indentation slopes of said tooth shaped portions of said rod.

5. The hypodermic syringe according to claim 1, characterized in that said cylindrical tubular body includes a longitudinal rib engageable by said blocking means to prevent rotation of the blocking means relative to said tubular body.

6. In a hypodermic syringe having a hollow cylindrical tubular body and piston means including a piston located within the tubular body and having a piston rod, the piston means being movable axially of the tubular body in one direction to retract the piston for drawing a substance into the tubular body and being movable in the opposite direction to advance the piston for discharging the substance, and the piston means being rotatable within the tubular body between first and second angular positions, the improvement comprising: blocking means including first means cooperating with the piston means to permit the piston to be retracted while the piston means is at said first angular position and to prevent subsequent advancement of the piston as long as the piston means remains at said first angular position, second means cooperating with the piston to permit advancement of the piston while the piston means is at said second angular position and to prevent subsequent retraction of the piston while the piston means remains at said second angular position; and locking means effective upon rotation of the piston means from said first angular position to said second angular position for preventing rotation of the piston means from said second angular position to said first angular position, said locking means comprising a disc member having an aperture conforming to the shape of said piston rod and adapted for rotation therewith, and resilient means coaxially positioned about said piston rod and including a locking arm which engages the disc member when said disc member is rotated to said second angular position.

7. The hypodermic syringe according to claim 6 wherein said locking means includes a guide notch associated with the disc member and stop means associated with the tubular body, said guide notch cooperating with said stop means to define said fist and second angular positions.

8. The hypodermic syringe according to claim 6 wherein said first means comprises a first lug associated with one of the piston means and the tubular body, and first ratchet means associated with the other one of the piston means and the tubular body, and wherein said second means comprises a second lug associated with one of the piston means and the tubular body, and second ratchet means associated with the other one of the piston means and the tubular body.

9. The hypodermic syringe according to claim 8 wherein said first and second ratchet means are associated with the piston means, said first ratchet means being located on a first side of the piston means and said second ratchet means being located on a second side of the piston means which is opposite to the first side.

10. The hypodermic syringe according to claim 9 wherein said first ratchet means comprises a first set of teeth on a first surface of the piston rod and extending axially of the piston rod and inclined in a first direction, and said second ratchet means comprises a second set of teeth on a second surface of the piston rod and extending axially of the piston rod and inclined in a direction opposite to said first direction.

11. The hypodermic syringe according to claim 8 wherein said first and second lugs are associated with the tubular body and are located spaced apart approximately 90° from one another within the tubular body.

12. The hypodermic syringe according to claim 11 wherein said blocking means comprises first and second angular members located within the tubular body and indexed thereto, said angular members having said first and second projections directed inwardly toward the axis of the tubular body, defining said first and second lugs, respectively.

13. The hypodermic syringe according to claim 11 wherein said blocking means comprises a one-piece angular member located within the tubular body and indexed thereto, said angular member having said first and second projections directed inwardly toward the axis of the tubular body, defining said first and second lugs, respectively.

14. In a hypodermic syringe having a hollow cylindrical tubular body and piston means including a piston located within the tubular body and having a piston rod, the piston means being movable axially of the tubular body in one direction to extend the piston with respect to the tubular body for drawing a substance into the tubular body and being movable in the opposite inward direction to advance the piston for discharging the substance from the distal end of the body, and the piston means being rotatable within the tubular body between first and second angular positions, the improvement comprising: first and second ratchet means on said piston means, blocking means positioned within said tubular body and including a first lug cooperating with first ratchet means to permit the piston means to be extended while the piston means is at said first angular position and to prevent subsequent advancement of the piston as long as the piston means remains at said first angular position and a second lug cooperating with second ratchet means to permit advancement of the piston while the piston means is at said second angular position and to prevent subsequent retraction of the piston while the piston means remains at said second angular position; and locking means associated with the piston means and effective upon rotation of the piston means from said first angular position to said second angular position for preventing further rotation of the piston means relative to the tubular body.

15. The hypodermic syringe according to claim 14 wherein said locking means includes a guide member associated with the piston means and adapted to cooperate with the tubular body for limiting rotational movement of the piston means.

16. The hypodermic syringe according to claim 15 wherein said locking means includes a resilient member cooperating with said guide member for preventing rotation of the piston means from said second angular position to said first angular position.

17. The hypodermic syringe according to claim 14 wherein said first ratchet means is located on a first side of the piston means and said second ratchet means is located on a second side of the piston means which is opposite to the first side.

18. The hypodermic syringe according to claim 17 wherein said first ratchet means comprises a first set of teeth on a first surface of the piston rod and extending axially of the piston rod and inclined in a first direction, and said second ratchet means comprises a second set of teeth on a second surface of the piston rod and extending axially of the piston rod and inclined in a direction opposite to said first direction.

19. The hypodermic syringe according to claim 14 wherein said first and second lugs are located spaced apart approximately 90° from one another.

* * * * *

UNITED STATES PATENT AND TRADEMARK OFFICE
CERTIFICATE OF CORRECTION

PATENT NO. : 5,250,030
DATED : October 5, 1993
INVENTOR(S) : Cesar G. Corsich

It is certified that error appears in the above-indentified patent and that said Letters Patent is hereby corrected as shown below:

In The Abstract

| LINE | |
|---|---|
| 7 | Delete "on" and insert -- one -- |

Signed and Sealed this

Twelfth Day of April, 1994

Attest:

BRUCE LEHMAN

Attesting Officer     Commissioner of Patents and Trademarks